(12) United States Patent
Al-Mutawaa

(10) Patent No.: US 8,741,353 B1
(45) Date of Patent: Jun. 3, 2014

(54) OINTMENT FOR HEALING BURNS AND WOUNDS

(71) Applicant: May Ghaith M. Al-Mutawaa, Qadsiya (KW)

(72) Inventor: May Ghaith M. Al-Mutawaa, Qadsiya (KW)

(*) Notice: Subject to any disclaimer, the term of this patent is extended or adjusted under 35 U.S.C. 154(b) by 0 days.

(21) Appl. No.: 14/165,137

(22) Filed: Jan. 27, 2014

(51) Int. Cl.
*A61K 35/64* (2006.01)
*A61K 36/328* (2006.01)
*A61K 36/906* (2006.01)
*A61K 36/00* (2006.01)

(52) U.S. Cl.
USPC ............ 424/539; 424/698; 424/748; 424/756; 424/776; 424/725

(58) Field of Classification Search
None
See application file for complete search history.

(56) References Cited

U.S. PATENT DOCUMENTS

| | | | |
|---|---|---|---|
| 4,587,124 A | 5/1986 | Kim | |
| 4,883,664 A | 11/1989 | Sharkey | |
| 5,350,774 A | 9/1994 | Palou | |
| 5,405,608 A | 4/1995 | Xu | |
| 6,099,866 A | 8/2000 | Slimak | |
| 6,673,755 B2* | 1/2004 | Wei et al. | 510/130 |
| 6,699,488 B2* | 3/2004 | Deckner et al. | 424/401 |
| 7,691,419 B2 | 4/2010 | DiLeva | |
| 2004/0101507 A1 | 5/2004 | Predovan | |
| 2006/0225285 A1* | 10/2006 | Slavtcheff et al. | 30/41 |
| 2007/0049512 A1* | 3/2007 | Keenan et al. | 510/439 |
| 2009/0068128 A1* | 3/2009 | Waddington | 424/59 |
| 2011/0159104 A1 | 6/2011 | Teslenko | |
| 2012/0308637 A1 | 12/2012 | Chamberland et al. | |
| 2013/0030341 A1 | 1/2013 | Freer et al. | |
| 2013/0251763 A1 | 9/2013 | Bettle, III | |

FOREIGN PATENT DOCUMENTS

| | | |
|---|---|---|
| CN | 101085092 A | 12/2007 |
| CN | 101757246 A | 6/2010 |
| GB | 2 338 413 A | 12/1999 |
| WO | WO 2011/113969 A1 | 9/2011 |

* cited by examiner

*Primary Examiner* — Chris R Tate
(74) *Attorney, Agent, or Firm* — Richard C Litman

(57) ABSTRACT

The ointment for healing burns and wounds includes a composition for treating skin burns, wounds, and other infection-prone skin complications. The composition includes honeycomb, sesame seed oil, myrrh, curcumin, mukul, and potassium alum. The ointment includes only natural ingredients that are unadulterated or minimally processed. Topical use of the ointment does not result in harmful side effects.

11 Claims, No Drawings

OINTMENT FOR HEALING BURNS AND WOUNDS

BACKGROUND OF THE INVENTION

1. Field of the Invention

The present invention relates to medicinal ointments, and particularly to a medicinal ointment for healing burns and wounds.

2. Description of the Related Art

Appropriate treatment of burns is necessary to minimize pain, avoid infection, and promote healing. Minor burns are typically treated with conventional drugs, including antiphlogistics, antiseptics or analgesics, to mitigate inflammation, prevent infection or relieve pain or discomfort of patients. More severe burns, however, cannot adequately be treated with conventional drugs alone. Severe burns, such as deep secondary and third degree burns, invade dermal and subcutaneous tissues, resulting in destruction of most of the follicles and sebaceous glands. Obvious scars appear after healing and usually affect function and outward appearance. As such, patients with deep secondary and third degree burns suffer greatly for an extended period, and often need skin grafts, in addition to conventional drugs.

Thus, an ointment for healing burns and wounds that may effectively treat burns of varying degrees of severity, is desired.

SUMMARY OF THE INVENTION

The ointment for healing burns and wounds includes a composition for treating skin burns and wounds. The composition includes honeycomb, sesame seed oil, myrrh, curcumin, mukul, and potassium alum. The composition may include only natural ingredients that are unadulterated or minimally processed. Topical use of the ointment does not result in harmful side effects.

These and other features of the present invention will become readily apparent upon further review of the following specification.

DETAILED DESCRIPTION OF THE PREFERRED EMBODIMENTS

The ointment for healing burns and wounds may be topically applied for effectively treating skin burns and wounds. The ointment includes effective amounts of honeycomb or wax sealed honeycomb cells, myrrh, curcumin, Balsamodendrum mukul ("mukul"), alum, and sesame seed oil. The ointment may be used to treat minor burns as well as severe burns. For example, the ointment may be used to treat first, second, and third degree burns. Skin wounds that may be treated with the ointment include any type of infection-prone skin complication, for example, cuts, boils, hair follicle infections, skin pus accumulations, blister, skin ulcers, bed sores, wound stitches, surgical dressings, canker sores, circumcision wounds, and cold sores on the lips and gum. Topical use of the ointment may heal the burn or wound and restore the skin. For example, application of the ointment on the affected skin may prevent infection, minimize pain, and restore the affected skin such that little or no scarring is visible on the restored skin.

The ointment for healing burns and wounds may include only natural ingredients. The natural ingredients may be unadulterated or minimally processed. The ointment may be stored for at least three years, without the use of preservatives.

Honeycomb may be the main natural ingredient of the ointment for healing burns and wounds. Honeycomb includes a mass of hexagonal wax cells containing honey. Preferably the honeycomb is fresh and includes at least some wax cells that are naturally sealed. The honeycomb may be eight weeks in age or less, for example. The honeycomb is preferably unbleached and includes honey of any natural color. The ointment may include all of the honeycomb or only a part of the honeycomb, i.e., only the wax sealed cells of the honeycomb.

Myrrh, curcumin, Balsamodendrum mukul ("mukul"), alum, and sesame seed oil are other natural ingredients which may be included in the ointment. Myrrh is the aromatic resin of a number of small, thorny tree species of the genus *Comiphora*. Myrrh resin is a natural gum. Myrrh has anti-inflammatory, antioxidant, and anti-microbial properties. Curcumin is a substance naturally found in turmeric. Curcumin has antioxidant and anti-inflammatory properties. Mukul, also called *Balsamodendron Mukulis, Commiphora wightii*, Guggal, and gum guggul, is a flowering plant in the family Burseraceae. Mukul has anti-arthritic and anti-inflammatory properties. A naturally-occurring alum particularly suitable for the ointment is potassium alum. Potassium alum or alum-(K) is a naturally occurring sulfate mineral which typically occurs as encrustations on rocks in areas of weathering and oxidation of sulfide minerals and potassium-bearing minerals. Potassium alum is useful to stop bleeding. Sesame seed oil is a useful oil for relieving dryness.

One or more of the natural ingredients described above may provide some benefit to skin affected by a burn or wound. For example, one or more of the natural ingredients may be effective for treating inflammation, relieving pain, and/or preventing infection to some degree. Collectively, however, the natural ingredients of the ointment provide enhanced benefits to the burned or wounded skin. In other words, the natural ingredients of the ointment act synergistically to provide increased effectiveness. For example, the ointment for healing burns and wounds may accelerate the healing time of the affected skin. Further, the ointment may effectively heal burns and wounds of various degrees of severity. In addition, the ointment for healing burns and wounds may significantly reduce inflammation during the healing period, prevent keloid formation, and minimize or eliminate the occurrence of any related scarring or discoloration of the skin.

Effective amounts of the natural ingredients in the ointment for healing skin burns and wounds are as follows: about 70% by weight to about 80% by weight honeycomb; about 10% by weight to about 20% by weight sesame seed oil; about 5% by weight to about 10% by weight curcumin; about 1% by weight to about 5% by weight myrrh; about 0.5% by weight to about 1% by weight mukul; and about 0.5% by weight to about 1% by weight potassium alum. As an example, about 630-850 grams of the ointment for healing burns and wounds may include a) about 1000 grams honeycomb or wax sealed honeycomb cells; b) about 220 ml of sesame seed oil; c) about 100 grams curcumin; d) about 30 grams myrrh; e) about 10 grams Balsamodendrum mukul; and f) about 10 grams potassium alum.

As discussed above, topical application of the ointment for healing skin burns and wounds may reduce the healing time of the affected skin. Preferably, the ointment is applied directly to the skin shortly after sustaining the burn or wound. For example, the ointment is preferably first applied to the skin within one to two hours after sustaining the burn or wound. However, the ointment may still be effective if applied to the skin several days after sustaining the burn or wound. Restoration of severely burned skin may generally be observable within twenty four hours of first application of the ointment for healing skin burns and wounds. Within one week of first application of the ointment for healing skin burns and wounds, the burn may be completely healed, without keloid formation or severe discoloration of the skin.

The ingredients of the present ointment are readily available and can be inexpensively mixed on a commercial scale in any suitable manner known in the art. A preferred methodology for making the ointment is provided below.

Example 1

Preparation of Ointment

About 100 grams of curcumin, about 30 grams of myrrh, about 10 grams of mukul, and about 10 grams of potassium alum, were each ground to achieve a grain size of about 1-2 millimeters. The curcumin, myrrh, mukul, and potassium alum were then combined to form a dry component mixture. About 1000 grams of honeycomb was cut into large cubes and placed into a cast iron container. The container was then placed in an electric oven for 30 minutes at 50° C. The dry component mixture was then mixed into the softened honeycomb with a wooden utensil to form a honeycomb mixture. The ingredients in the honeycomb mixture were mixed for about two minutes and then placed in a cast iron container and heated in an electric oven for 24 hours at 50° C. About 220 mL of sesame seed oil was then mixed into the honeycomb mixture and left to simmer in the electric oven for 2 hours at 50° C. The mixture was then poured onto a very fine cotton mesh for filtering. The filtered mixture was then mixed with an electric mixer on medium to high speed for five minutes to obtain a homogeneous mixture.

Example 2

Use of Ointment

A male patient with severe burns and inflammation on his hand was treated with the ointment. The affected area of the hand was cleaned. A gauze pad, containing a thin layer of the ointment, was placed over the affected area and wrapped with layers of dry gauze. The ointment was applied to the burn in this manner twice a day. After four days of application of the ointment, inflammation of the hand had subsided and skin appeared smooth with only minor discoloration. After one week of application of the ointment, the skin was completely restored with significantly reduced discoloration.

It is to be understood that the present invention is not limited to the embodiments described above, but encompasses any and all embodiments within the scope of the following claims.

I claim:

1. A skin ointment comprising:
   a) about 70% by weight to about 80% by weight honeycomb;
   b) about 10% by weight to about 20% by weight sesame oil;
   c) about 5% by weight to about 10% by weight curcumin;
   d) about 1% by weight to about 5% by weight myrrh;
   e) about 0.5% by weight to about 1% by weight mukul; and
   f) about 0.5% by weight to about 1% by weight alum.

2. The skin ointment according to claim 1, wherein the honeycomb comprises wax cells.

3. The skin ointment according claim 1, wherein the honeycomb is unbleached.

4. The skin ointment according to claim 1, wherein the honeycomb comprises honey.

5. A method of making a skin ointment, comprising:
   a) combining curcumin, myrrh, mukul, and alum to form a dry component mixture;
   b) pre-heating honeycomb until soft;
   c) combining the dry component mixture with the pre-heated honeycomb to form a honeycomb mixture;
   d) heating the honeycomb mixture in a container;
   e) adding sesame oil to the heated honeycomb mixture to form a final mixture;
   f) heating the final mixture; and
   g) mixing the final mixture to form the skin ointment.

6. The method of claim 5, wherein components of the dry component mixture comprise granules having a grain size of about 1 mm to about 2 mm.

7. The method of claim 5, wherein the honeycomb is pre-heated for about 30 minutes at 50° C.

8. The method of claim 5, wherein the honeycomb mixture is heated for about 24 hours at 50° C.

9. The method of claim 5, wherein the final mixture is heated for 2 hours at 50° C.

10. The method of claim 5, wherein:
    a) the dry component mixture is formed by combining about 100 grams curcumin, about 30 grams myrrh, about 10 grams mukul, and about 10 grams alum;
    b) the honeycomb mixture is formed by combining about 1000 grams of honeycomb with the dry component mixture; and
    c) the final mixture is formed by adding about 220 ml of sesame oil to the honeycomb mixture.

11. A method for treating burned or wounded skin, comprising applying to the skin an ointment comprising:
    a) about 70% by weight to about 80% by weight honeycomb;
    b) about 10% by weight to about 20% by weight sesame oil;
    c) about 5% by weight to about 10% by weight curcumin;
    d) about 1% by weight to about 5% by weight myrrh;
    e) about 0.5% by weight to about 1% by weight mukul; and
    (f) about 0.5% by weight to about 1% by weight alum.

* * * * *